(12) United States Patent
Audeh et al.

(10) Patent No.: US 12,716,104 B2
(45) Date of Patent: Aug. 25, 2026

(54) SAMPLE POOLING ASSAY

(71) Applicant: Verily Health Inc., Dallas, TX (US)

(72) Inventors: Mark Audeh, Brookline, MA (US); Eric Paoli, Los Altos, CA (US); Bradley White, Burlingame, CA (US); Dorothea Duong, Milpitas, CA (US); Manali Dwarakanath, Fremont, CA (US); Vikram Chan-Herur, San Francisco, CA (US); Aaron Topol, Mountain View, CA (US)

(73) Assignee: Verily Health Inc., Dallas, TX (US)

( * ) Notice: Subject to any disclaimer, the term of this patent is extended or adjusted under 35 U.S.C. 154(b) by 312 days.

(21) Appl. No.: 18/580,079

(22) PCT Filed: Jul. 14, 2022

(86) PCT No.: PCT/US2022/073720
§ 371 (c)(1),
(2) Date: Jan. 17, 2024

(87) PCT Pub. No.: WO2023/004253
PCT Pub. Date: Jan. 26, 2023

(65) Prior Publication Data
US 2025/0277279 A1 Sep. 4, 2025

Related U.S. Application Data

(60) Provisional application No. 63/223,398, filed on Jul. 19, 2021.

(51) Int. Cl.
*C12Q 1/70* (2006.01)
*C12Q 1/6851* (2018.01)

(52) U.S. Cl.
CPC .......... *C12Q 1/701* (2013.01); *C12Q 1/6851* (2013.01)

(58) Field of Classification Search
None
See application file for complete search history.

(56) References Cited

U.S. PATENT DOCUMENTS 10,378,008 B2 * 8/2019 Roth .................... C12Q 1/686
2008/0015112 A1 1/2008 Fors et al.
2017/0211058 A1 7/2017 Roth et al.

OTHER PUBLICATIONS

Wacharapluesadee et al., Evaluating the efficiency of specimen pooling for PCR-based detection of COVID-19, J Med Virol. Jul. 21, 2020;92(10):2193-2199. doi: 10.1002/jmv.26005.*
International Patent Appl. No. PCT/US2022/073720, International Search Report and the Written Opinion, Oct. 4, 2022, 9 pages.
Singapore Appl. No. 11202400240U, Written Opinion, dated Oct. 20, 2025.
Abdalhamid, et al., "Cost Effectiveness of Sample Pooling to Test for SARS-CoV-2", The Journal of Infection in Developing Countries, vol. 14, No. 10, Oct. 31, 2020, pp. 1136-1137.
Alcoba-Florez, et al., "Increasing SARS-CoV-2 RT-QPCR Testing Capacity by Sample Pooling", International Journal of Infectious Diseases, vol. 103, Nov. 19, 2020, pp. 19-22.

(Continued)

*Primary Examiner* — Aaron A Priest
(74) *Attorney, Agent, or Firm* — Kilpatrick Townsend & Stockton LLP

(57) ABSTRACT

Provided herein are compositions and methods for detecting nucleic acids in pooled samples.

23 Claims, 2 Drawing Sheets

(56) References Cited

OTHER PUBLICATIONS

Ben-Ami, "Large-Scale Implementation of Pooled RNA Extraction and RT-PCR for SARS-CoV-2 Detection", Clinical Microbiology and Infection, vol. 26, No. 9, Jun. 23, 2020, pp. 1248-1253.

Bruinsma, et al., "Bead-Linked Transposomes Enable a Normalization-Free Workflow for NGS Library Preparation", BMC Genomics, vol. 19, No. 1, Oct. 1, 2018, pp. 1-16.

Europe Appl. No. 22846755.1, Extended European Search Report, Sep. 1, 2025, 15 pages.

Kendziorski, et al., "On the Utility of Pooling Biological Samples in Microarray Experiments", Proceedings of the National Academy of Sciences (PNAS), vol. 102, No. 12, Mar. 22, 2005, pp. 4252-4257.

Molinari, et al., "Sample Pooling and Inflammation Linked to the False Selection of Biomarkers for Neurodegenerative Diseases in Top-Down Proteomics: A Pilot Study", Frontiers in Molecular Neuroscience, vol. 11, Article No. 477, Dec. 18, 2018, pp. 1-10.

Praharaj, et al., "Pooled Testing for Covid-19 Diagnosis by Real-time RT-PCR : A Multi-site Comparative Evaluation of 5- & 10-Sample Pooling", Indian Journal of Medical Research, vol. 152, No. 1-2, Jul. 1, 2020, pp. 88-94.

* cited by examiner

SAMPLE POOLING ASSAY

CROSS-REFERENCE TO RELATED APPLICATIONS

This application claims the benefit of U.S. Provisional Application No. 63/223,398, filed Jul. 19, 2021, which is hereby incorporated herein by this reference in its entirety.

BACKGROUND

Current protocols for pooled sample testing are time-consuming and expensive. In existing approaches to pooled sample testing, the standard input sample volume of the test sample (for example, 100 μL) is composed of smaller volume samples (for example, 10 μL from 10 individuals for a single 100 μL input). These direct pooling methods have sensitivity limitations. As the number of samples in the pool is increased, each individual sample is diluted, reducing the sensitivity of the overall test. This trade-off between sensitivity and pooling number limits the size of the pool, and is never as sensitive as a single test run without a pooling approach. There is a need for compositions and methods to facilitate inexpensive and sensitive pooled sample testing.

SUMMARY

The Summary is provided to introduce a selection of concepts that are further described below in the Detailed Description. This Summary is not intended to identify key or essential features of the claimed subject matter, nor is it intended to be used as an aid in limiting the scope of the claimed subject matter.

Provided herein is a method for detecting the presence of a nucleic acid in a pooled sample. Therefore, the methods provided herein can be used to detect a nucleic acid in a plurality of samples, for example, biological samples, that are pooled. In some embodiments, the nucleic acid is a pathogen nucleic acid, for example, a viral nucleic acid. In some embodiments, the method comprises the steps of adding lysis buffer to a pooled sample to create a solution pool, wherein the pooled sample comprises two or more non-diluted, test samples, and wherein the lysis buffer is added in an amount proportional to the number of individual samples. Next, nucleic acid binding beads are added to the solution pool, wherein when the pooled sample comprises up to about 100 test samples, the amount of nucleic acid binding beads added is the amount used to analyze a single, individual test sample and this amount increases proportionately for every additional 100 samples or fraction thereof in the pooled sample. Then, the nucleic acid binding beads are concentrated in the solution pool before separating the nucleic acid binding beads from the solution pool and washing the nucleic acid binding beads. Finally, the nucleic acid binding beads are analyzed to detect the presence or absence of a nucleic acid.

In some methods, detecting the presence of a nucleic acid in the pooled sample further comprises collecting non-diluted test samples, for example, from at least two or more individuals, and pooling the two or more non-diluted individual test samples to create the pooled sample, prior to lysing the pooled sample. In some methods, the nucleic acid can be DNA or RNA. In some methods, the RNA is SARS-COV-2 RNA. In some methods, the pooled sample comprises cells from nasal swabs of five or more individuals.

In some methods, the lysis buffer contains a buffering salt and/or an ionic salt and may further comprise a detergent. In some methods, the buffering salt of the lysis buffer is selected from a group consisting of MPS, DPS, Tris-HCl, and HEPES-NaOH. In some methods, the ionic salt is selected from a group consisting of NaCl, KCl, and $(NH_4)_2SO_4$. In some methods, the lysis buffer further comprises a detergent. In some methods, the detergent is selected from a group consisting of Triton X-100, TWEEN, and CHAPS.

In some methods, the separation step comprises magnetic separation, centrifugation, or column filtration. In some methods, analyzing comprises polymerase chain reaction (PCR). In some methods, PCR comprises quantitative or endpoint PCR.

In some methods, analyzing further comprises sequencing the nucleic acid adhered to the nucleic acid binding beads. In some methods, the nucleic acid adhered to the beads is eluted for the analyzing step.

Any of the methods of detecting the presence of a nucleic acid in a pooled sample, for example, a pathogen nucleic acid, can further comprise obtaining a test sample from the at least two or more individuals, if the nucleic acid is detected in the pooled sample, and detecting the presence of the nucleic acid in one or more of the individual test samples. In some methods the nucleic acid is a viral nucleic acid.

DESCRIPTION OF THE FIGURES

The present application includes the following figures. The figures are intended to illustrate certain embodiments and/or features of the compositions and methods, and to supplement any description(s) of the compositions and methods. The figures do not limit the scope of the compositions and methods, unless the written description expressly indicates that such is the case.

DETAILED DESCRIPTION

Figure 1:
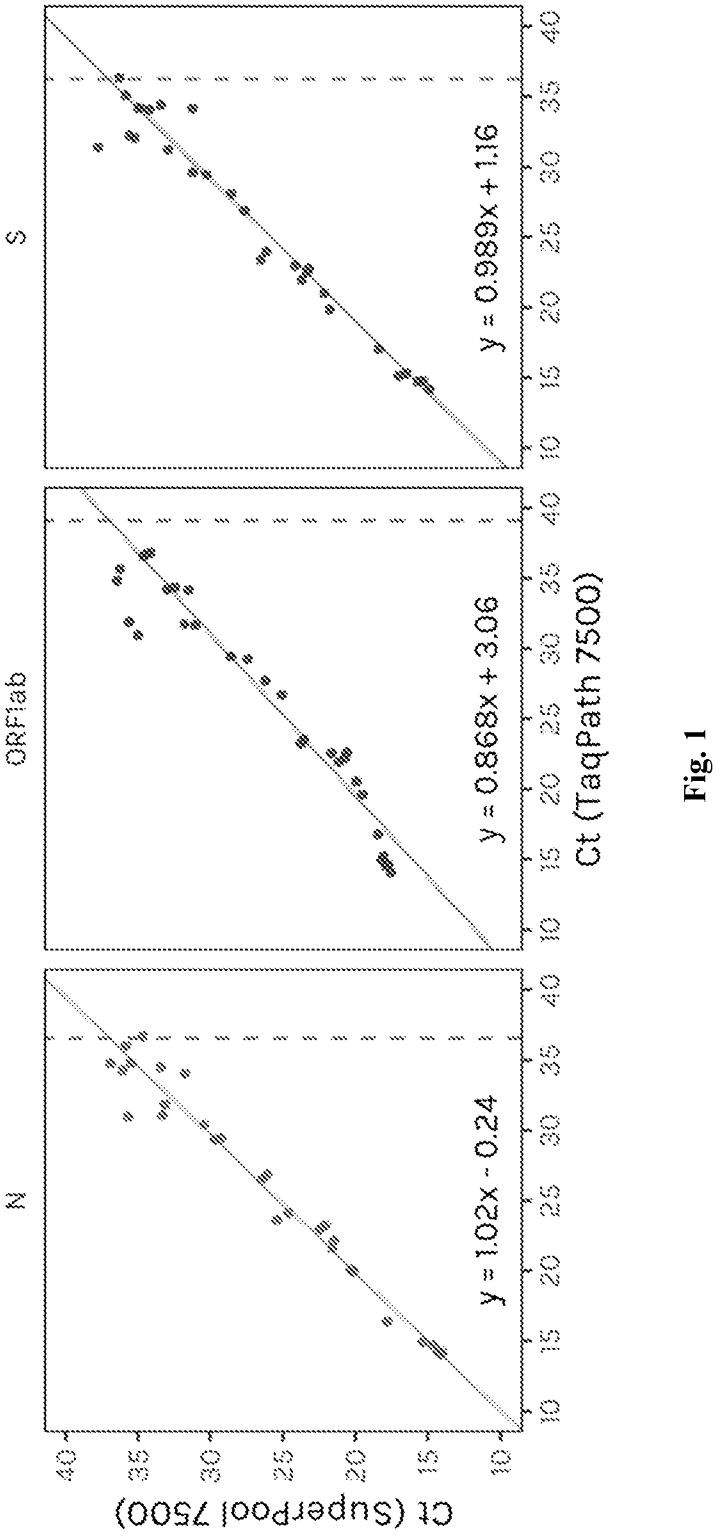
FIG. 1 shows the results of analyzing 100-plex pools of 1 positive upper respiratory sample and 99 negative upper respiratory samples analyzed by the ThermoFisher TaqPath™ Combo Kit EUA and super pooling methods on the 7500 Fast Dx. The diagonal line is the Passing-Bablok regression line; the vertical dashed line shows the equivalent TaqPath™ Ct when the regression equation (displayed on chart) is solved for a pooled Ct of 37.

The following description recites various aspects and embodiments of the present compositions and methods. No particular embodiment is intended to define the scope of the compositions and methods. Rather, the embodiments merely provide non-limiting examples of various compositions and methods that are at least included within the scope of the disclosed compositions and methods. The description is to be read from the perspective of one of ordinary skill in the art; therefore, information well known to the skilled artisan is not necessarily included.

Individually screening large populations for rare pathogens can be wasteful and expensive. To solve this problem, sample pooling methods to improve the efficiency of large-scale pathogen screening campaigns have been developed. These methods aim to reduce the number of tests and reagents required to accurately categorize positive and negative individuals. Such methods rely on group testing theory, which mainly focuses on minimizing the total number of tests per population subset. The most widely-used assays for viral testing of these sample pools involves polymerase chain reaction (PCR). PCR methods vastly increase the number of nucleic acid molecules, thereby amplifying the target sequence(s) in a patient sample. However, because these tests are expensive and require trained personnel, high frequency, widely distributed testing is still prohibitively expensive. Further, these issues are exacerbated during viral pandemics because throughput limitations and material constraints become additional barriers to sufficient widespread testing.

Provided herein are compositions and methods for rapidly and sensitively detecting a nucleic acid of interest in pooled samples. Any DNA or RNA of interest can be detected. In some embodiments, the nucleic acid is pathogen nucleic acid, for example, a viral nucleic acid, a bacterial nucleic acid, or a fungal nucleic acid, to name a few.

As set forth above, existing PCR approaches to pooled sample nucleic acid testing have limitations because each, individual sample, in a pooled sample, is diluted, thus reducing the sensitivity of the overall test. This trade-off between sensitivity and pooling number limits the size of the pool, and by definition is never as sensitive as a single test run without a pooling approach.

The methods described herein overcome the limitations caused by dilution. These methods also remove throughput limitations and materials constraints of present PCR-based pooled sample testing, for example, for viral testing. Provided herein is a pooling assay for the qualitative detection of nucleic acid from pooled samples. In some embodiments, these samples include respiratory swab specimens from individuals suspected of COVID-19. In some examples, detection is achieved using reverse transcription PCR (RT-PCR), without specimen dilution, by adding nucleic acid binding beads to the pooled sample at an amount equivalent to a the amount used in a single reaction. The beads allow for DNA/RNA concentration from the pooled samples into a single PCR reaction without dilution of the input target. By eliminating the dilution of target nucleic acids, the loss in sensitivity normally incurred due to pooling is circumvented. Since the binding capacity of the binding beads is high, there is no significant difference in sensitivity between a single reaction and a pool comprising samples from 100 or more individuals. In addition, there are no additional reagents or concentration steps required that differ from the standard workflow other than volume changes at the lysis and binding steps. The results are practical and provide regulatory benefits in viral testing.

Provided herein is a method for detecting the presence of a nucleic acid in a pooled sample, the method comprising the steps of: (a) adding lysis buffer to a pooled sample to create a solution pool, wherein the pooled sample comprises two or more non-diluted test samples, and wherein the lysis buffer is added in an amount proportional to the number of individual samples; (b) adding nucleic acid binding beads to the solution pool, wherein, when the pooled sample comprises up to about 100 test samples, the amount of nucleic acid binding beads added is the amount used to analyze a single, individual test sample and this amount increases proportionately for every additional 100 samples or fraction thereof in the pooled sample; and (c) analyzing the nucleic acid binding beads to detect the presence or absence of the nucleic acid. Some methods further comprise concentrating the nucleic acid binding beads in the solution pool; separating the nucleic acid binding beads from the solution pool; and/or washing the nucleic acid binding beads prior to analyzing the nucleic acid binding beads to detect the presence or absence of the nucleic acid.

Provided herein is a method for detecting the presence of a viral nucleic acid in a pooled sample, the method comprises, consists of, or consists essentially of, the steps of: (a) adding lysis buffer to a pooled sample to create a solution pool, wherein the pooled sample comprises non-diluted test samples from at least two or more individuals, and wherein the lysis buffer is added in an amount proportional to the number of individual samples; (b) adding nucleic acid binding beads to the solution pool, wherein the amount of nucleic acid binding beads wherein, when the pooled sample comprises up to about 100 test samples, the amount of nucleic acid binding beads added is the amount used to analyze a single, individual test sample and this amount increases proportionately for every additional 100 samples or fraction thereof in the pooled sample; (c) concentrating the nucleic acid binding beads in the solution pool; (d) separating the nucleic acid binding beads from the solution pool; (e) washing the nucleic acid binding beads; and (f) analyzing the nucleic acid binding beads to detect the presence or absence of the viral nucleic acid.

In some embodiments, the number of samples is at least two to about one hundred samples and the amount of nucleic acid binding beads is about the amount (1×) used to analyze a single, individual sample. In some embodiments, the number of samples is at least one hundred to about one thousand samples and the amount of nucleic acid binding beads is about two times (2×) to about ten times (10×) the amount used to analyze a single, individual sample.

In some embodiments, non-diluted test samples are collected from at least two or more individuals and the two or more individual test samples are pooled to create a pooled sample, prior to lysing the pooled sample. As used herein, a "pooled sample" refers to a sample resulting from combining two or more collected samples from individuals, which allows for more individuals to be tested using fewer testing resources. As used herein, a "single" or individual" test sample refers to a sample collected from an individual before it is pooled. The single or individual sample is not diluted prior to pooling. It is understood that a non-diluted sample, can be the entire, original volume (full volume) of solution in which the sample from the subject was placed or a sub-sample (i.e., an aliquot) from the original, non-diluted sample obtained from the subject. For example, if a nasal swab obtained from the subject is placed in 1 ml of sample solution, the entire 1 ml sample or a sub-sample, for example, 20 μL to 400 μL of the 1 ml solution containing the nasal swab, can be used as the non-diluted, full volume test sample that is subsequently pooled. The individual, non-diluted test sample volume can be any volume, for example, about 1, 5, 10, 15 20, 30, 40, 50, 60, 70, 80, 90, 100, 110, 120, 130, 140, 150, 200, 250, 300, 350, 400, 450, 500, 550, 600, 650, 700, 750, 800, 850, 900, 1000 μL or greater. In some methods, the volume can be from about 20-400 μL, for example, from about 30 μL to about 400 μL. In some methods, for example, when using the ThermoFisher TaqPath™ Combo Kit, the sample volume can be about 200 μL to about 400 μL, for example, about 200, 250, 300, 350 or 400 μL. For example, in some methods, non-diluted test samples can be collected from at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, or 200 individuals, and pooled. In some methods, full volume test samples are collected from at least 200, 225, 250, 275, 300, 325, 350, 375, 400, 450, 500, 550, 600, 650, 700, 750, 800, 850, 900, 950, 1000 or more individuals, and then pooled.

As used throughout, the terms "individual" and "subject" are used interchangeably. The subject can be an adult subject or a pediatric subject. Pediatric subjects include subjects ranging in age from birth to eighteen years of age. Preferably, the subject is an animal, for example, a mammal such as a primate, and, more preferably, a human. Non-human primates are subjects as well. The term subject includes domesticated animals, such as cats, dogs, etc., livestock (for example, cattle, horses, pigs, sheep, goats, etc.) and laboratory animals (for example, ferret, chinchilla, mouse, rabbit, rat, gerbil, guinea pig, etc.). Thus, veterinary uses are contemplated herein.

The invention provides methods of detecting nucleic acids, for example, nucleic acids from microorganisms, within samples. As will be appreciated by those of skill in the art, the sample may comprise any number of sources, including, but not limited to, bodily fluids of virtually any organism, and environmental samples (including, but not limited to, air, agricultural, water and soil samples). In addition, samples can be taken from food processing, which can include both input samples (e.g. grains, milk or animal carcasses), samples in intermediate steps of processing, as well as finished food ready for consumption.

As used throughout, a sample can be any biological sample, for example, blood, nasal cells/fluid, urine, serum, lymph, saliva, anal and vaginal secretions, perspiration, peritoneal fluid, pleural fluid, effusions, ascites, and purulent secretions, lavage fluids, drained fluids, brush cytology specimens, biopsy tissue, explanted medical devices, infected catheters, pus, biofilms or semen. In some methods, a throat swab, cheek swab, or nasal swab is immersed or contacted with the sample. In some embodiments, a plurality of samples comprising non-diluted test samples from two or more individuals can be provided to, and analyzed by, systems, devices, and methods disclosed herein. Methods, devices and systems disclosed herein are configured to perform multiple assays on a sample, or on a plurality of sample types, and may be used to screen for one or more pathogens. Methods, devices and systems disclosed herein are configured to perform multiple assays on a sample, or on a plurality of sample types, and may be used to detect one or more of viruses, bacteria, yeast, fungus, *mycoplasma*, archaea, fungus, yeast, parasites, and other micro-organisms.

As used herein, the term "virus" or "viral" refers to any of a large group of infections entities that cannot grow or replicate without a host cell. Viruses typically contain a protein coat surrounding an RNA or DNA core of genetic material, but no semipermeable membrane, and are capable of growth and multiplication only in living cells. Thus, a virus is a packaged viral genome, capable of transferring nucleic acids into cells either in vitro or in vivo. As used herein, "viral replication" is the production of additional virus by the occurrence of at least one viral life cycle. In the methods provided herein, viral DNA and/or RNA can be detected. In some embodiments, the virus is SARs-COV-2. In some embodiments, the virus is selected from the group consisting of adenovirus, influenza A (all subtypes), influenza B (all subtypes), parainfluenza, rhinovirus, enterovirus, metapneumovirus, respiratory syncytial virus, bocavirus, coronavirus (for example, HKU1, NL63, 229E and OC43). As set forth above, the methods provided herein can be used to pool and detect any RNA or DNA of interest, for example, a bacterial nucleic acid, a fungal nucleic acid, a parasitic nucleic acid, to name a few.

As used herein, "viral nucleic acid" refers to viral genetic material encoded in DNA or RNA. Viral nucleic acids can be double-stranded or single-stranded, monopartite or multipartite, linear or circular. Viral nucleic acids detected using the methods provided herein can be from about 0.1 kb to about 2500 kb in size, or larger.

As used throughout, the term "nucleic acid" or "nucleotide" refers to deoxyribonucleic acids (DNA) or ribonucleic acids (RNA) and polymers thereof in either single- or double-stranded form. It is understood that when an RNA is described, its corresponding DNA is also described, wherein uridine is represented as thymidine. Unless specifically limited, the term encompasses nucleic acids containing known analogues of natural nucleotides that have similar properties as the reference nucleic acid and are metabolized in a manner similar to naturally occurring nucleotides. A nucleic acid sequence can comprise combinations of deoxyribonucleic acids and ribonucleic acids. Such deoxyribonucleic acids and ribonucleic acids include both naturally occurring molecules and synthetic analogues. The polynucleotides of the invention also encompass all forms of sequences including, but not limited to, single-stranded forms, double-stranded forms, hairpins, stem-and-loop structures, and the like.

Unless otherwise indicated, a particular nucleic acid sequence also implicitly encompasses modified variants thereof, alleles, orthologs, SNPs, and complementary sequences as well as the sequence explicitly indicated.

In the methods provided herein, 90%, 95%, 99% or more of the non-diluted, test sample can be added to the pool of samples to be tested, so as not to significantly dilute the non-diluted test sample. In other words, if a non-diluted test sample of at least 25 μL, 50 μL, 75 μL, 100 μL or more is used, at least 90%, 95%, 99% or more of the sample is added to the pool to created a pooled sample. In some embodiments, 100% of the non-diluted sample is added to the sample pool. As an example, if a nasal swab from each of two individuals is placed into 200 μL of sample buffer, each 200 μL sample, i.e., a non-diluted sample, is added to the sample pool, to create a 400 μL pooled sample comprising the non-diluted test samples of the two individuals. In another example, if a nasal swab from each of ten individuals is placed into 200 μL of sample buffer, each 200 μL sample, i.e., a full volume sample, is added to the sample pool, to create a 2000 μL pooled sample comprising the non-diluted test samples of ten individuals. In another example, a nasal swab from each of ten individuals can be placed into 1 ml sample buffer, and 50 μL (i.e., a subsample or aliquot) from each 1 ml sample can be pooled to create a 500 μL solution pool comprising ten, non-diluted, test samples. These examples are merely illustrative as one of skill in the art would know that the methods provided herein can be adapted depending on the amount of the non-diluted sample for each individual and the number of individuals to be tested using the pooled sample.

One of skill in the art will understand that the amount of the non-diluted test sample will vary, depending on numerous factors, such as PCR method, reagents, pathogen, etc. However, as long as the amount of lysis buffer added to the pooled sample is proportional to the number of individual samples, i.e., the volume or amount of lysis buffer added to the pooled sample is the amount normally added for a single non-diluted sample, multiplied by the number of samples. For example, if a non-diluted 100 μL test sample is normally lysed with 100 μL of lysis buffer, then, a pooled sample (500 μL) comprising five non-diluted 100 μL test samples would be lysed with 500 μL of lysis buffer, or 5 times the amount of lysis buffer used for a single sample. Similarly, if a non-diluted 100 μL test sample is normally lysed with 50 μL of lysis buffer, then, a pooled sample (1000 μL) comprising ten non-diluted 100 μL test samples would be lysed with 500 μL of lysis buffer, or ten times the amount of lysis buffer used for a single sample. For example, using a ThermoFisher TaqPath™ Combo Kit EUA 200 μL input volume protocol, 265 μL of lysis buffer is used for an individual sample. Therefore, a pooled sample of 100 individual samples would require 2650 μL of lysis buffer.

As used herein, "lysis buffer" refers to a buffer solution used for the purpose of breaking open cells contained in a sample to release genetic material encoded in DNA and/or RNA found inside the cell. Any lysis buffer that is suitable for lysing the cell membrane and nuclear membrane of a cell(s) or populations of cells, while maintaining the integrity of the nucleic acid (i.e., protecting DNA or RNA from lysis), as it separates the nucleic acid from other cell debris, can be used in the methods provided herein. In some embodiments, the lysis buffer comprises a buffering salt and/or an ionic salt. As used herein, a "buffering salt" refers to a salt that fixes excess amounts of acid or alkali, measured in pH, without a change in hydrogen ion concentration. As used herein, an "ionic salt" refers to a salt added to a buffer solution to maintain a desired or preferred ionic strength.

In some embodiments, the buffering salt is selected from a group consisting of: MPS, DPS, Tris-HCl, and HEPES-NaOH. In some embodiments, the ionic salt is selected from a group consisting of: NaCl, KCl, and $(NH_4)_2SO_4$. In some methods, the lysis buffer can optionally comprise a detergent. In some embodiments, the detergent is selected from a group consisting of: Triton X-100, Triton-X114, NP-40, Brij-35, Brij-58, Tween 20, Tween 80, Octyl glucoside, Octyl thioglucoside, sodium dodecyl sulfate (SDS), CHAPS, guanidinium thiocyanate and CHAPSO, to name a few.

In any of the methods provided herein, once the samples are lysed to create a solution pool, nucleic acid binding beads are added the solution pool. It is understood that the binding beads are not added in an amount proportional to the number of samples. As shown herein, the same amount of binding bead solution having the binding capacity to detect a nucleic acid in single sample can be used to detect a nucleic acid in a pooled sample comprising up to 100 samples. For example, if 10-20 μL of binding bead solution are normally used to analyze a single sample, if there are 100 individual samples in the pooled sample, only 10-20 μL of binding bead solution would be added to the pooled sample, and not 1000-2000 μL (i.e, 100 samples×10-20 μL). In other words, the same amount of binding bead solution would be added to a pooled sample comprising two samples as a pooled sample comprising fifty samples, or a pooled sample comprising one hundred samples. The amount of binding bead solution added increases proportionately with every additional 100 samples or fraction thereof added to the pooled sample.

Generally, the amount added to a pooled solution including up to 100 non-diluted test samples, is about the amount of binding bead solution used to detect a specific nucleic acid in a single, individual sample. When the pooled sample comprises more than 100 samples, for every additional one hundred samples or fraction thereof, the amount of nucleic acid binding beads added to the solution increases proportionately. For example, the amount of binding beads added to the pooled sample including about 200 non-diluted test samples will be about 2× the amount added to the pooled sample comprising up to 100 non-diluted test samples. Similarly, the amount of binding beads added to the pooled sample including about 300 non-diluted test samples will be about 3× the amount added to the pooled sample comprising up to 100 samples.

The amount of binding beads will vary depending on the size of the pooled sample, the binding capacity of the nucleic acids per bead and/or the bead concentration in the bead solution added to the solution pool. The amount of beads necessary to analyze a single, individual sample can be the amount indicated by the manufacturer for any kit now known or available in the future for detecting a nucleic acid of interest in a single sample. This amount can also be determined by one of skill in the art. In some embodiments, the kit is the ThermoFisher TaqPath™ Combo Kit EUA (ThermoFisher, Waltham, MA).

For example, in some embodiments, when the number of samples is from about one hundred to about one thousand samples, the amount of binding beads will vary between about one-time to about 10-times the amount of beads used to analyze a single sample. In some embodiments, the amount of beads is between about 1× and 2× (e.g., for about one hundred to two hundred samples), from about 2× to 3× (e.g., for about two hundred to about three hundred samples), from about 3× to 4× (e.g., for about three hundred to about four hundred samples), from about 4× to 5× (e.g., for about four hundred to about five hundred samples), from about 5× to 6× (e.g., for about five hundred to about six hundred samples), from about 6× to 7× (e.g., for about six hundred to about seven hundred samples), from about 7× to 8× (e.g., for about seven hundred to about eight hundred samples), from about 8× to 9× (e.g., for about eight hundred to about nine hundred samples) or from about 9× to 10× (e.g., for about nine hundred to about one thousand) the number of beads used to analyze a single sample. For pooled samples of greater than 1,000 samples, for example, 2,000, 3,000, 4,000, 5,000, 6,000, 7,000, 8,000, 9,000, or 10,000 samples, 20× the number of beads used to analyze a single sample or greater can be used. For example, when using the Fisher TaqPath™ Combo Kit EUA 200 μL protocol, 10 μL of binding beads are used to analyze a single sample. Therefore, 10 μL of binding beads would be added to a 2000 μL pooled sample comprising ten, 200 μL samples, and about 100 μL of binding beads would be added to analyze a pooled sample comprising one thousand, 200 μL samples. In another example, when using the Fisher TaqPath™ Combo Kit EUA 400 μL protocol, 20 μL of binding beads are used to analyze a single sample. Therefore, 20 μL of binding beads would be added to a 4000 μL pooled sample comprising ten, 400 μL samples, and about 200 μL of binding beads would be added to analyze a pooled sample comprising one thousand, 400 μL samples.

Once the nucleic acid in the solution pool is bound by the beads, the beads are concentrated, separated and washed. The beads are then analyzed to detect the presence or absence of the nucleic acid. In any of the methods provided herein the nucleic acid beads can be concentrated or separated via magnetic separation or centrifugation.

In the methods provided herein, the beads can be concentrated, for example, by centrifugation, and resuspended in appropriate amount of a sample buffer, for example, about 20 μL to about 100 μL of a sample buffer suitable for further analysis. In some embodiments, pooling of about 5 to about 100 samples occurs, and analysis is conducted without the concentration step, i.e., without concentrating the beads.

The nucleic acid binding beads used in the methods provided herein have high efficiency nucleic acid binding surfaces and can be separated from the solution through a variety of methods. In one embodiment, an exemplary bead high efficiency nucleic acid binding surface can be, but is not limited to, silica beads, magnetic nucleotide binding beads, resins (for example, size exclusion resins, positively charged matrices, or nucleic acid hybridization probes. The methods provided herein are not limited to a specific binding bead or resin as any nucleic acid binding surface that can separate DNA or RNA from a solution pool can be used In particular, the nucleic acid binding surface, e.g., a bead or resin, should be efficient at binding DNA or RNA, easily slurred in a large volume sample and capable of being concentrated, for example, by magnetic capture, centrifugation or other means of bead/resin capture. In some embodiments, the beads can be separated from solution via magnetic separation. In some embodiments, the beads can be separated from solution via centrifugation.

In yet another embodiment, and without excluding other possible separation methods known in the art, the beads can be separated from solution through column filtration. In some embodiments, the beads are separated from the solution pool without concentrating the beads.

As used herein, "magnetic separation" refers to a separation method that uses a magnetic field to separate paramagnetic particles from a suspension. As used herein, "centrifugation" refers to a method of separation of particles (for example, beads) from a solution where the sample is placed in a rotor and spun at a defined speed to separate the particles according to their size, shape, density, and viscosity of the medium.

In some embodiments, the nucleic acid adhered to the beads can be analyzed on the beads. The beads, which are roughly equivalent in number to those found in a single standard reaction according to the isolation method or kit chosen, contain DNA and/or RNA from all pooled samples and can be directly placed into a single reaction of a standard quantitative or end point PCR workflow. As set forth above, the separated beads can be resuspended in about 20 μL to about 100 μL of a sample buffer. In one exemplary embodiment, the standard quantitative or end point PCR workflow can be, but is not limited to, TaqPath™ (ThermoFisher)

In some embodiments, the nucleic acid adhered to the beads can be eluted into an elution buffer for example, about 5 μL to about 100 μL of a sample buffer suitable for further analysis. In the methods provided herein, the nucleic acid beads or nucleic acid eluted from the beads can be analyzed to detect a viral nucleic acid, for example, a SARS-COV-2 nucleic acid.

The analyzing step can comprise amplification of the nucleic acid. As used herein, "amplification" of an amplifiable nucleic acid molecule (e.g., a DNA or RNA viral nucleic acid) refers to use of a laboratory technique that increases the number of copies of nucleic acid molecules in a sample, such as PCR. As used herein, the term "amplifiable nucleic acid" is used in reference to nucleic acids that may be amplified by any amplification method. It is contemplated that "amplifiable nucleic acid" will usually comprise a nucleic acid "target region."

As used herein, the term "target," or "target nucleic acid sequence" refers to a nucleic acid sequence or structure to be detected or characterized. Thus, the "target" or "target nucleic acid sequence" is sought to be sorted out or identified from other nucleic acid sequences. Examples of "targets" or "target nucleic acid sequences" include, but are not limited to, viral nucleic acid sequences, for example, viral RNA sequences (e.g. from SARS COV-2).

The process for amplification of a desired nucleic acid sequence can be achieved by any means known in the art, for example, via polymerase chain reaction (PCR). Exemplary PCR techniques include, but are not limited to, endpoint PCR, real-time PCR (quantitative PCR or qPCR), reverse-transcriptase PCR (RT-PCR), multiplex PCR, nested PCR, and high fidelity PCR. See, or example, Eftekhari et al. "A Comprehensive Review of Detection Methods for SARS-COV-2," *Microorganisms* 2021, 9, 232. The primers and probes for amplification can be purchased or prepared by any means known in the art, including automated processes. In some embodiments, the primers and probes are designed for specificity for the target nucleic acid sequence, as disclosed herein.

As used herein, the term "primer" refers to an oligonucleotide, whether occurring naturally as in a purified restriction digest or produced synthetically, which is capable of acting as a point of initiation of synthesis when placed under conditions in which synthesis of a primer extension product which is complementary to a nucleic acid strand is induced, (i.e., in the presence of nucleotides and an inducing agent such as DNA polymerase and at a suitable temperature and pH). The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer should be sufficiently long to prime the synthesis of extension products in the presence of the inducing agent. The exact lengths of the primers will depend on many factors, including temperature, source of primer and the use of the method.

As used herein, the terms "PCR product," "PCR fragment," and "amplification product" refer to the resultant mixture of compounds after two or more cycles of the PCR steps of denaturation, annealing and extension are complete. These terms encompass the case where there has been amplification of one or more segments of one or more target sequences.

As used herein, "quantitative PCR" refers to a quantitative technique that looks at the exponential phase of PCR by using fluorescent probes that increase in abundance, or intensity, with the amplification product. During the exponential phase of PCR the target DNA doubles in a 100% efficient mixture during each PCR cycle because all reagents are fresh and available during this phase of the PCR reaction.

As used herein, "endpoint PCR" refers to a quantitative technique in PCR that determines the amount of template DNA at the start of the reaction by looking at how much is present at the end of a reaction.

In any of the methods provided herein, analyzing can comprise sequencing the nucleic acid adhered to the nucleic acid binding beads or the nucleic acid eluted from the nucleic acid beads. Sequencing methods include, but are not limited to, shotgun sequencing, bridge PCR, Sanger sequencing (including microfluidic Sanger sequencing), pyrosequencing, massively parallel signature sequencing, nanopore DNA sequencing, single molecule real-time sequencing (SMRT) (Pacific Biosciences, Menlo Park, CA), ion semiconductor sequencing, ligation sequencing, sequencing by synthesis (Illumina, San Diego, Ca), Polony sequencing, 454 sequencing, solid phase sequencing, DNA nanoball sequencing, heliscope single molecule sequencing, mass spectroscopy sequencing, pyrosequencing, Supported Oligo Ligation Detection (SOLID) sequencing, DNA microarray sequencing, RNAP sequencing, tunneling currents DNA sequencing, and any other DNA sequencing method identified in the future. One or more of the sequencing methods described herein can be used in high throughput sequencing methods. As used herein, the term "high throughput sequencing" refers to all methods related to sequencing nucleic acids where more than one nucleic acid sequence is sequenced at a given time.

If the presence of the nucleic acid is detected in a pooled sample, using the methods set forth herein, the pooled sample is positive for the nucleic acid, for example, a viral nucleic acid. If the absence of a viral nucleic acid is detected in any of a pooled sample, using the methods set forth herein, the pooled sample is negative for the viral nucleic acid. For any of the methods provided herein, if a pooled sample comprising individual samples from two or more individuals is positive for the viral nucleic acid, the methods can further comprise obtaining a second test sample from the at least two or more individuals and detecting the presence of the viral nucleic acid in one or more of the individual test samples. This allows identification of the one or more individuals from the pooled sample who are positive for the viral nucleic acid. Once the one or more individuals are identified, the one or more individuals can be treated for the viral infection, quarantined, and/or referred for medical attention.

As used herein, the articles "a" and "an" are used herein to refer to one or to more than one (i.e. at least one) of the grammatical object of the article. By way of example, "an element" means at least one element and can include more than one element.

The term "about" is used to provide flexibility to a numerical range endpoint by providing that a given value may be "slightly above" or "slightly below" the endpoint without affecting the desired result.

The use herein of the terms including, comprising, or having, and variations thereof, is meant to encompass the elements listed thereafter and equivalents thereof as well as additional elements. Embodiments recited as including, comprising, or having certain elements are also contemplated as consisting essentially of and consisting of those certain elements. As used herein, and/or, refers to and encompasses any and all possible combinations of one or more of the associated listed items, as well as the lack of combinations where interpreted in the alternative ("or").

As used herein, the transitional phrase "consisting essentially of" (and grammatical variants) is to be interpreted as encompassing the recited materials or steps "and those that do not materially affect the basic and novel characteristic(s)" of the claimed invention. See, *In re Herz,* 537 F.2d 549, 551-52, 190 U.S.P.Q. 461, 463 (CCPA 1976) (emphasis in the original); see also MPEP § 2111.03. Thus, the term "consisting essentially of" as used herein should not be interpreted as equivalent to "comprising."

Recitation of ranges of values herein are merely intended to serve as a shorthand method of referring individually to each separate value falling within the range, unless otherwise-Indicated herein, and each separate value is incorporated into the specification as if it were individually recited herein. For example, if a concentration range is stated as 1% to 50%, it is intended that values such as 2% to 40%, 10% to 30%, or 1% to 3%, etc., are expressly enumerated in this specification. These are only examples of what is specifically intended, and all possible combinations of numerical values between and including the lowest value and the highest value enumerated are to be considered to be expressly stated in this disclosure.

Disclosed are materials, compositions, and components that can be used for, can be used in conjunction with, can be used in preparation for, or are products of the disclosed methods and compositions. These and other materials are disclosed herein, and it is understood that when combinations, subsets, interactions, groups, etc. of these materials are disclosed that while specific reference of each various individual and collective combinations and permutations of these compounds may not be explicitly disclosed, each is specifically contemplated and described herein. For example, if a method is disclosed and discussed and a number of modifications that can be made to a number of molecules including in the method are discussed, each and every combination and permutation of the method, and the modifications that are possible are specifically contemplated unless specifically indicated to the contrary. Likewise, any subset or combination of these is also specifically contemplated and disclosed. This concept applies to all aspects of this disclosure including, but not limited to, steps in methods using the disclosed compositions. Thus, if there are a variety of additional steps that can be performed, it is understood that each of these additional steps can be performed with any specific method steps or combination of method steps of the disclosed methods, and that each such combination or subset of combinations is specifically contemplated and should be considered disclosed.

Publications cited herein and the material for which they are cited are hereby specifically incorporated by reference in their entireties.

EXAMPLES

Example 1: Pooling, Extraction, Detection, and Analysis of SARS-COV-2 RNA from Upper Respiratory Swab Specimens The Super Pooling assay is a real-time reverse transcription polymerase chain reaction (RT-PCR) test intended for the qualitative detection of nucleic acid from pooled SARS-COV-2 in upper respiratory swap specimens from individuals suspected of COVID-19.

Sample Preparation

If the specimen was frozen, the specimen tube was completely thawed at room temperature. Then, the specimen tubes were vortexed using a VWR® Multi-Tube Vortexer (Avantor, Radnor, PA) for 30 seconds, and centrifuged, at 2,000×g, for 1 minute.

Decap Samples

The Pluggo™ Decapper (LGP Consulting wood River, IL) was prepared according to the manufacturer's instructions. Up to 24 tubes were loaded onto the Pluggo carousel in the Biological Safety Cabinet (BSC), prior to loading the carousel onto the Pluggo Decapper. The shield was lowered and the instrument was run to start decapping. The decapping cycle is complete after the carousel cycles through one complete revolution (or 24 positions). Next, when the Pluggo has stopped, the shield was raised to remove the carousel from the instrument. Inside the BSC, up to 32 samples were transferred to a Tecan Fluent ID™ tube runner (Tecan, Mannedorf, Switzerland). Samples on the tube runner were placed starting from the position furthest away from the handle.

Pool Samples

To generate pools, a Tecan Fluent® GX automated liquid handler (using Tecan FluentControl v2.6 software) was used. The Tecan Fluent® GX automated liquid handler was prepared according to manufacturer's instructions. On the "Method Starter" screen the "C19 Super Pooling" method was selected. The run parameters were entered: left, right, or both arms and number of samples. The on-screen prompt was followed for placement of disposable tips and 50 mL Falcon tube(s). Sample tubes were added when specifically prompted by the FluentID scanning dialogs. When disposable tips and 50 mL Once Falcon tubes were added to the worktable, liquid transfers began. During method execution the liquid handler transferred 200 μL of each sample into a 50 mL Falcon tube. When done, the source tubes were removed from the worktable, recapped, and stored.

Binding Bead Solution

The Binding Bead Solution was prepared by vortexing the MagMAX™ Viral/Pathogen (ThermoFisher Scientific, Waltham, MA) Binding Beads at max speed for 10 seconds. An appropriate amount of Binding Bead Mix were prepared in an appropriate container, as seen in Table 1, and mixed by inversion 5 times.

TABLE 1

| Volumes for Binding Bead Mix | | | | | | |
|---|---|---|---|---|---|---|
| Component | Single Reaction Volume | Volume for n Samples in Pool | Volume for 23 Samples in Pool | Volume for 31 Samples in Pool | Volume for 46 Samples in Pool | Volume for 93 Samples in Pool |
| Binding Solution | 265 μL | 265 × n μL | 6.095 mL | 8.215 mL | 12.190 mL | 24.645 mL |
| Binding Beads | 20 μL | 20 μL | 20 μL | 20 μL | 20 μL | 20 μL |
| Total Volume | 285 μL | 265 × n + 20 μL | 6.115 mL | 8.235 mL | 12.210 mL | 24.665 mL |

Next, 5 μL of MS2 Phage Control was added to each 50 mL Falcon Pool tube. An appropriate amount of Proteinase K was then added to each 50 mL Falcon tube, as defined in Table 2.

TABLE 2

| Volumes for Proteinase K | | | | | | |
|---|---|---|---|---|---|---|
| Component | Single Reaction Volume | Volume for n Samples in Pool | Volume for 23 Samples in Pool | Volume for 31 Samples in Pool | Volume for 46 Samples in Pool | Volume for 93 Samples in Pool |
| Proteinase K | 5 μL | 5 × n μL | 115 μL | 155 μL | 230 μL | 465 μL |

Each 50 mL Falcon tube was then vortexed at maximum speed for 5 seconds. The appropriate amount of Binding Bead Mix, depending on the number of samples in each pool, was then added in each of the 50 mL Falcon tubes, according to Table 1. Next, each 50 mL Falcon tube was vortexed at maximum speed for five seconds. Following, the 50 mL Falcon tube was placed on the Eppendorf ThermoMixer C with the Eppendorf SmartBlock™ 50 mL adapter, set at 60° C. for 20 minutes, at 1,000 RPM. Each 50 mL Falcon tube was vortexed at maximum speed for five seconds. Next, the 50 mL Falcon tube were centrifuged at 4,200 RPM for 5 minutes to pellet the beads.

Next, the Falcon tubes were placed in a magnetic stand. A 50 mL serological pipette was then positioned at the center of the tube to carefully decant the supernatant without disrupting the bead pellet. In case the bead pellet was disrupted during decanting, the supernatant was placed back into the 50 mL Falcon tube and the process of centrifugation and pellet formation were repeated. Once the supernatant was successfully decanted without disrupting the bead pellet, the bead pellet was resuspended with any remaining supernatant. The resuspended supernatant was then transferred into a new KingFisher™ Deep Well Plate.

Preparation of KingFisher™ Plates

The elution solution intermediate plates were prepared by adding aliquots of 6 mL of elution solution into a reagent reservoir. Next, a multi-channel pipette was used to aliquot 60 μL of Elution Solution into each well of the Elution Intermediate Plate. A Microseal B Adhesive Seal or MicroAmp Clear Adhesive Film was used to seal the plate, and the plate was then centrifuged for 1 minute at 2,000×g.

Next, the Agilent software and protocol were prepared according to manufacturer instructions (Agilent, Santa Clara, CA). Then, the "Elution Solution Plate Stamp" VWorks form was used. The number of elution plates to stamp were set up and the Agilent Bravo deck was prepared according to the desired layout. Once all Bravo positions are specified, then the Bravo deck was run. During the protocol, the Agilent Bravo transferred 50 μL of Elution Solution to each well of each "Elution Plate." Once the protocol was complete, the "Elution Solution Plate(s)" were sealed with a Microseal B Adhesive Seal or MicroAmp Clear Adhesive Film. All consumables were then removed from the Bravo and discarded.

Next, a 80% ethanol plate was prepared by mixing absolute ethanol and Molecular Biology Grade Water (MBGW) in a 250 ml conical tube, according to Table 3. The well was mixed by inversion 5 times.

TABLE 3

| Volumes for 80% Ethanol | | |
|---|---|---|
| Component | Single Reaction Volume | Volume for 1 KingFisher Extraction Plate |
| Absolute Ethanol | 0.8 mL | 120 mL |
| Molecular Biology Grade Water | 0.2 mL | 30 mL |
| Total Volume | 1 mL | 150 mL |

The BioTek MultiFlo FX (Biotek, Santa Clara, CA) was prepared according to manufacturer instructions. Then, a 10 μL dispense cassette was loaded on the primary peri-pump, ensuring that the tubing was routed properly around the peri-pump. The 80% ethanol conical tube was secured in a bottle holder and the peri-pump tubing was inserted so that the end rested at the bottom of the conical tube with the 80% ethanol. The "80% Ethanol Plate" was loaded into the nest. Next, the protocol primed 1 mL of 80% ethanol through each dispense tube and a small volume of ethanol was dispensed into the priming trough at the end of this step. Following, the protocol dispensed 1 mL of 80% ethanol to each well of the "80% Ethanol Plate." When the dispense cycle was complete, the "80% Ethanol Plate" was removed from the nest. The "80% Ethanol Plate" was then sealed with a Microseal B Adhesive Seal or MicroAmp Clear Adhesive Film. The purging protocol emptied the remaining 80% ethanol back into the source bottle. Once plate processing was complete, a cleaning protocol followed. The wash buffer was prepared according to Table 4.

TABLE 4

| Volumes for Wash Buffer | | |
|---|---|---|
| Component | Single Reaction Volume | Volume for 1 KingFisher Extraction Plate |
| Wash Buffer | 1 mL | 150 mL |

RNA Extraction on the KingFisher

First, the KingFisher Flex Magnetic Particle Processor with the 96 Deep-Well Head was set up with the KingFisher Flex 96 Deep-Well heating block. The "SuperPooling" program was run and the prepared plates were loaded into position, when prompted by the instrument. After the run was complete, the "Elution Plate" was immediately removed from the instrument, and the plate was covered with a Microseal B Adhesive Seal or MicroAmp Clear Adhesive Film.

RT-PCR for the 7500 Fast Dx

If reagents were frozen, the were thawed on ice. Following, the reagents were gently vortexed and centrifuged briefly to collect liquid at the bottom of the tube. To prepare the reaction mixture, for each run, the components were combined according to Table 5, sufficient for the number of columns to be processed in an Eppendorf DNA LoBind® ⅕ mL tube. The reaction mix volumes accounts for controls.

TABLE 5

| 96-Well Reaction Mix Volumes | | | | | | | |
|---|---|---|---|---|---|---|---|
| Component | Single Reaction Volume | Volume for 1 Column | Volume for 2 Columns | Volume for 3 Columns | Volume for 4 Columns | Volume for 6 Columns | Volume for 12 Columns |
| TaqPath ™ 1-Step Multiplex Master Mix (No ROX ™) (4X) | 6.25 μL | 260 μL | 310 μL | 360 μL | 410 μL | 510 μL | 760 μL |
| COVID-19 Real Time PCR Assay Multiplex | 1.25 μL | 52 μL | 62 μL | 72 μL | 82 μL | 102 μL | 152 μL |
| Total Reaction Mix Volume | 7.50 μL | 312 μL | 372 μL | 432 μL | 492 μL | 612 μL | 912 μL |

Next, a new Eppendorf LoBind® 96-well Plate was labeled as the "Master Mix" plate and the appropriate amount of Reaction Mix was aliquoted, according to Table 6, to each well of the "Master Mix" plate. The Reaction Mix was transferred to column 1 of the "Master Mix" plate, regardless of the number of columns, for processing.

TABLE 6

| Reaction Plate Volumes for 7500DX Setup | | | |
|---|---|---|---|
| Component | # Columns for Processing | Column or Well Position | Volume per Well |
| Reaction Mix | 1 | Col1 | 35 μL |
| | 2 | | 42.5 μL |
| | 3 | | 50 μL |
| | 4 | | 57.5 μL |
| | 6 | | 72.5 μL |
| | 12 | | 110 μL |
| TaqPath ™ COVID-19 Control Dilution Buffer | 1-4 | A5 | 200 μL |
| TaqPath ™ COVID-19 Control | 1-4 | B5 | 10 μL |
| Molecular Biology Grade Water | 1-4 | C5 | 100 μL |

To set-up the reaction plate, the Agilent Bravo software protocol was prepared according to manufacturer's instructions. In the VWorks program, the desired protocol was selected, as were the desired number of columns for processing from the drop-down menu (options range from 1, 2, 3, 4, 6, or 12). The Bravo deck was set up as desired. To run Bravo, all Bravo positions were verified before beginning the program. During the protocol, the Bravo transferred 7.5 μL of reaction mix to each plate and control well. Serially, the protocol diluted the TaqPath™ COVID-19 Control from $1*10^4$ copies/μL to a working stock of 2.86 copies/μL. A 17.5 μL amount of diluted TaqPath™ COVID-19 Control was then transferred into well F12 of the reaction plate and mixed. Next, 17.5 μL of Molecular Biology Grade Water was transferred into well G12 of the reaction plate and mixed. When complete, all other consumables were removed from the Bravo and discarded.

Next, samples were transferred into the reaction plate. The sealed plate(s) containing the purified sample RNA and Negative Control from the RNA extraction procedure were vortexed for 10 seconds and then the plate is centrifuged for 1 minute at 2,000×g to collect liquid at the bottom of the plate. The Agilent software and protocol was prepared, as described above. The protocol was run through the VWorks program and the number of columns was selected (the options were 1, 2, 3, 4, 6, or 12). Once the Bravo deck was prepared, a new Agilent LT 250 tip box was placed in Position 1, while making sure that the Reaction Plate from the master mix transfer was still on Position 6, on top of the 96-well black carrier.

All Bravo positions were verified, as specified, the protocol was run. During the protocol Bravo prompted the user to "place the KingFisher DW Plate at Position 9, unseal the purified RNA sample plate(s) containing the purified sample RNA and Negative Control from the RNA extraction procedure and place the plate(s) on Position 9. Next, Bravo prompted the user to "Remove and discard 2 tips from Position F12 and G12 of the Tip Box at *BRAVO DECK POSITION 1 ONLY*. Following, sample transfer began where 17.5 μL of sample or Negative Control from the purified RNA sample plates were transferred into the reaction plate and mixed. Once VWorks indicated the protocol was complete, the reaction plate was removed from the Bravo deck. The reaction plate was sealed thoroughly with MicroAmp™ Optical Adhesive Film.

Next, the reaction plate was vortexed at the highest setting speed for 15 seconds, with medium pressure, and the plate was moved around to ensure equal contact on the vortexer. The plate was centrifuged for 1 minute at 2,000×g. Next, the purified sample RNA was sealed with a Microseal B Adhesive Seal or MicroAmp Clear Adhesive Film. Store the plate at −80° C.

Sample Transfer

The sealed RT-PCR Reaction Plate was transferred on a chilled cold block to Post-PCR lab. All samples were allowed to air dry.

RT-PCR for QuantStudio 5

If frozen, reagents were thawed on ice. The reagents were gently vortexed and then centrifuged briefly to collect liquid at the bottom of the tube. The Reaction Mix was then prepared by combining components sufficient for the number of plates to be processed, according to Table 7, for each run. For 1 plate, use an Eppendorf DNA LoBind® 1.5 mL Tube. For 2 plates, use an Eppendorf DNA LoBind® 2.0 mL Tube. For 3 or 4 plates, use an Eppendorf DNA LoBind® 5.0 mL Tube.

TABLE 7

384-Well Reaction Mix Volumes

| Component | Single Reaction Volume | Volume for 1 Plate | Volume for 2 Plates | Volume for 3 Plates | Volume for 4 Plates |
|---|---|---|---|---|---|
| TaqPath ™ 1-Step Multiplex Master Mix (No ROX ™) (4X) | 6.25 L | 760 μL | 1495 μL | 2230 μL | 2960 μL |
| COVID-19 Real Time PCR Assay Multiplex | 1.25 L | 152 μL | 299 μL | 446 μL | 592 μL |
| Total Reaction Mix Volume | 7.50 L | 912 μL | 1794 μL | 2676 μL | 3552 μL |

A new Eppendorf LoBind® 96-well Plate was labeled "Master Mix" plate. Table 8 outlines the appropriate amount of Reaction Mix to be aliquoted to each well of the "Master Mix" plate. If processing 1 plate, transfer Reaction Mix to column 1 of the "Master Mix" plate. If processing 2 plates, transfer Reaction Mix to columns 1 and 2 of the "Master Mix" plate. If processing 3 plates, transfer Reaction Mix to columns 1, 2, and 3 of the "Master Mix" plate. If processing 4 plates, transfer Reaction Mix to columns 1, 2, 3, and 4 of the "Master Mix" plate.

TABLE 8

Reaction Plate Volumes for QuantStudio 5 Setup

| Component | # Plates for Processing | Column or Well Position | Volume per Well |
|---|---|---|---|
| Reaction Mix | 1 | Col 1 | 110 μL |
| | 2 | Col 1 & 2 | |
| | 3 | Col 1-3 | |
| | 4 | Col 1-4 | |
| TaqPath ™ COVID-19 Control Dilution Buffer | 1-4 | A5 | 200 μL |

TABLE 8-continued

| Reaction Plate Volumes for QuantStudio 5 Setup | | | |
|---|---|---|---|
| Component | # Plates for Processing | Column or Well Position | Volume per Well |
| TaqPath ™ COVID-19 Control | 1-4 | B5 | 10 μL |
| Molecular Biology Grade Water | 1-4 | C5 | 100 μL |

Setup the Reaction Plate

The Agilent software and protocol was prepared as described above. Using the VWorks program, 1-4 samples plates were entered and the Bravo deck was set-up. The Bravo deck was prepared by following a predefined layout where the silver 384-well plate was inserted on Position 6. A new Agilent LT 250 tip box was placed on Position 2 and an empty Agilent LT 250 tip box was placed on Position 3. The "Master Mix" plate (Eppendorf LoBind 96-well Plate) was placed on Position 5.

When the Bravo protocol was run, 7.5 μL of reaction mix was transferred to each sample and control well. The TeqPath™ COVID-19 Control was serially diluted from $1*10^4$ copies/μL to a working stock of 2.86 copies/μL. 17.5 μL of diluted TeqPath™ COVID-19 Control were transferred into well K23 of the reaction plate and mixes. 17.5 μL of Molecular Biology Grade Water were transferred into well M23 of the reaction plate and mixes. When VWorks indicated the protocol was complete the reaction plate was left on Position 6 for the protocol.

Next, the sealed plate(s) containing the purified sample RNA and Negative Control from the RNA extraction procedure were vortexed for 10 seconds. Then, the plate was centrifuged for 1 minute of 2,000 rpm to collect liquid at the bottom of the plate. The Agilent software protocol was prepared as described above. From the VWorks program, the relevant protocol was opened and r the number of sample plates for processing were entered (with selection of options 1-4). The Bravo deck was prepared and new Agilent LT 250 tip boxes were set on the Bravo deck. For 1 plate, place a new Agilent LT 250 tip box on Position 1. For 2 plates, place new Agilent LT 250 tip boxes on Position 1 and Position 2. For 3 plates, place new Agilent LT 250 tip boxes on Position 1, Position 2, and Position 3. For 4 plates, place new Agilent LT 250 tip boxes on Position 1, Position 2, Position 3, and Position 4.

Next, it was ensured that the Reaction Plate from the master mix transfer is still on Position 6 on top of the silver 384-well plate insert. Next, all Bravo positions were verified before the the process began. During the protocol, Bravo prompted the user to "place the KingFisher DW Plate at Position 9." To do this, the user unsealed the purified RNA sample plate(s) containing the purified sample RNA and Negative Control from RNA extraction procedure. Next, the plate(s) were placed on Position 9 and this was repeated until all plates were loaded. Next, Bravo prompted the user to "Remove and discard 2 tips from Positions F12 and G12 of the Tip Box at *BRAVO DECK POSITION 1 ONLY*. Next, Bravo prompted the user to transfer 17.5 μL of sample of Negative Control from the purified RNA sample plates into the reaction plate and mix. Once VWorks indicated the protocol is complete, the reaction plate was removed from the Bravo deck and the Reaction Plate was sealed with PlateLoc Clear Peelable Seal (Agilent, Santa Clara, CA) using the PlateLoc at 160° C. for 3 seconds.

Next, the Reaction Plate was vortexed at the highest setting speed for 15 seconds, with medium pressure, and the plate was moved around to ensure equal contact on the vortexer. Then, the plate was centrifuged for 1 min at 2,000×g. The purified sample RNA was then sealed with a Microseal B Adhesive Seal or MicroAmp Clear Adhesive Film and stored at −80° C. The sample was then transferred from the RT-PCR Reaction Plate to the Post-PCR lab following carefully outlined decontaminating guidelines.

The 7500 Fast Dx Real-Time PCR Instrument

The run settings in the template were set as a standard curve assay (absolute quantitation), with a standard 7500 run mode, with no passive reference, and a sample volume of 25 μL. With the quencher set to none, detectors were set, according to Table 9.

TABLE 9

| Reporter Dyes and Detectors | |
|---|---|
| Reporter Dye | Detector |
| FAM | ORF1ab |
| VIC | N gene |
| ABY | S gene |
| JUN | MS2 |

Next, it was confirmed that the targets above were assigned to each well in the plate layout. The control wells included: (1) a template with one positive control (PC) and one negative control (NC) assigned to wells for reference, and (2) move the control well assignment by copying the existing control wells and pasting them according to their location on the physical plate. For wells with a positive control, the detectors were set to standard. For wells with a negative control, the detectors were set to no template control (NTC). For wells with a patient sample, all detectors were set to unknown. Wells that do not have a sample were not analyzed by the software.

The thermal protocol was set according to Table 10.

TABLE 10

| Thermocycler Program for RT-qPCR | | | | |
|---|---|---|---|---|
| Steps | Cycle #s | Temp (° C.) | Time | Purpose |
| 1 | 1 | 25 | 2 min | UNG incubation |
| 2 | 1 | 53 | 10 min | Reverse transcription |
| 3 | 1 | 95 | 2 min | Activation |
| 4 | 40x | 95 | 3 sec | Denaturation |
| 5 | | 60 | 30 sec | Anneal / extension |

Quantstudio 5 Real-Time PCR System

Using the QuantStudio Design and Analysis Desktop Software (ThermoFisher), the appropriate EDT file was selected, and the plate layout file was downloaded. In the Method tab, the thermal protocol was confirmed, as seen in Table 11:

TABLE 11

| Thermocycler Program for RT-qPCR | | | | |
|---|---|---|---|---|
| Steps | Cycle #s | Temp (° C.) | Time | Purpose |
| 1 | 1 | 25 | 2 min | UNG incubation |
| 2 | 1 | 53 | 10 min | Reverse transcription |
| 3 | 1 | 95 | 2 min | Activation |
| 4 | 40x | 95 | 3 sec | Denaturation |
| 5 | | 60 | 30 sec | Anneal / extension |

In the Targets table, the reporter dye and tart pairs were confirmed as correct, as seen in Table 12:

TABLE 12

| Reporter Dyes, Detectors, and Quenchers | | |
|---|---|---|
| Reporter Dye | Detector | Quencher |
| FAM | ORF1ab | None |
| VIC | N gene | None |

TABLE 12-continued

| Reporter Dyes, Detectors, and Quenchers | | |
|---|---|---|
| Reporter Dye | Detector | Quencher |
| ABY | S gene | None |
| JUN | MS2 | None |

It was confirmed that all targets above were assigned to each well in the plate layout. For all targets in the positive control well, confirm that Task is set to S (Standard) and for all targets in the negative control well, confirm that Task is set to N (Negative Control). For all targets in the no template control well, confirm that Task is set to U (Unknown). For wells with patient samples, Task should be set to U (unknown) for all targets. Names that do not have a sample name will not be analyzed by the software. Finally, load the 384-well reaction plate into the instrument and run the protocol.

Post-Processing Analysis

All test controls were assessed prior to interpretation of patient results. If controls were not valid, the patient results could not be interpreted. Any target with a Ct≤37 is positive and any target with a Ct>37 is negative, see Table 13 for a summary of the control results:

TABLE 13

| Expected Results of Controls | | | | |
|---|---|---|---|---|
| | Ct Value | | | |
| Control | N Gene | S Gene | ORF1ab | MS2 Phage |
| Negative Extraction Control | Undetermined[1] | Undetermined[1] | Undetermined[1] | ≤37 |
| Positive Control | ≤37 | ≤37 | ≤37 | Undetermined[2] |
| No Template Control | Undetermined[1] | Undetermined[1] | Undetermined[1] | Undetermined[2] |
| MS2 Internal Control | Any | Any | Any | ≤37 |

[1]Undetermined (Not detectable Ct; negative)

[2]The MS2 Phage Internal Control is not added to the Positive Control or No Template Control and no signal should be obtained.

Examination and Interpretation of Pooled Sample Results

Assessment of clinical specimen test results were performed after the positive and negative controls were examined and determined to be valid and acceptable. If the controls were not valid, the patient results were not interpreted, see Table 14.

TABLE 14

| Interpretation of Sample Pools | | | | | | |
|---|---|---|---|---|---|---|
| ORF1ab | N gene | S gene | MS2 | Status | Result | Action |
| NEG[1] | NEG[1] | NEG[1] | NEG[1] | Invalid | NA | Individually assay samples in the invalid pool starting from extractions (Step 9). |
| NEG[1] | NEG[1] | NEG[1] | POS Ct ≤ 37 | Valid | SARS-CoV-2 Not Detected in Pool | Deconvolution not required for samples in this pool. Report as presumptive negative. |
| Only one SARS-CoV-2 target = POS Ct ≤ 37 | | | POS or NEG[1] | Valid | SARS-CoV-2 Inconclusive in Pool | Deconvolute by individually assaying samples in the inconclusive pool.[2] |

TABLE 14-continued

| Interpretation of Sample Pools | | | | | | |
|---|---|---|---|---|---|---|
| ORF1ab | N gene | S gene | MS2 | Status | Result | Action |
| Two or more SARS-CoV-2 targets = POS Ct ≤ 37 | | | POS or NEG[1] | Valid | SARS-CoV-2 Detected in Pool | Deconvolute by individually assaying samples in the positive pool.[2] |

[1]NEG (Not detectable Ct; negative)

[2]If an inconclusive or positive pool exhibits amplification curves that indicate a 'false positive' or 'false inconclusive' the pool may be retested prior to deconvolution. If the retest of the pool is negative then the results will be reported as presumptive negative for samples in the pool without further reflex testing. If the retest is inconclusive or positive then the pool will be deconvoluted by individually assaying samples in the pool.

Example 2: Testing of Upper Respiratory Swab Specimens from Individuals Suspected of COVID-19 Through Quantitative Detection of Nucleic Acid from SARS-COV-2

The Super Pooling Assay is a real-time reverse transcription polymerase chain reaction (RT-PCR) test for the qualitative detection of nucleic acid from SARS-COV-2 in upper respiratory swab specimens from individuals suspected of COVID-19 by their healthcare provider. Super Pooling allows for up to 100 samples to be pooled into a single well with little to no loss in sensitivity as compared to TaqPath 200 μL EUA.

Evaluating the Limit of Detection (LoD) of the Super Pooling Assay

The LoD study established the lowest SARS-COV-2 viral concentration (Genomic Copy Equivalents or GCE) that can be detected by the Super Pooling assay in a particular specimen type.

Criteria for Success

At least 95% (19 out of the 20) of the LoD replicates must be identified as positive.

Results

The LoD of the Super Pooling assay was determined using quantified, SARS-COV-2 virus and SARS-COV-2 viral genomic RNA material obtained from ATCC (VR-1986D). A preliminary LoD was determined by testing a range of concentrations, in triplicate, at 1000 GCE/mL, 500 GCE/mL, 187.5 GCE/mL, 125 GCE/mL, 62.5 GCE/mL of spiked SARS-COV-2 virus, and spiked SARS-COV-2 viral genomic RNA into a matrix of pooled negative upper respiratory samples, extracted with the MagMAX kit on the KingFisher Flex instrument, and tested on both the Applied Biosystems 7500 Fast Dx and QuantStudio 5 real-time PCR, instruments using the same extracted RNA. The results for the preliminary LoD are shown in Table 15.

TABLE 15

| Preliminary LoD | | | | | | | | | | | | | | |
|---|---|---|---|---|---|---|---|---|---|---|---|---|---|---|
| | | SARS-CoV-2 N Gene Positive | | | SARS-CoV-2 S Gene Positive | | | SARS-CoV-2 ORF1ab Positive | | | MS2 (Internal Control Positive) | | |
| Target Level | Replicates | n | Mean $C_t$ | Detection Rate | n | Mean $C_t$ | Detection Rate | n | Mean $C_t$ | Detection Rate | n | Mean $C_t$ | Detection Rate |
| 7500 Dx Virus | | | | | | | | | | | | | |
| 1000 GCE/mL | 3 | 3 | 30.2 | 3/3 | 3 | 31.5 | 3/3 | 3 | 30.1 | 3/3 | 3 | 22.5 | 3/3 |
| 500 GCE/mL | 3 | 3 | 30.1 | 3/3 | 3 | 30.8 | 3/3 | 3 | 29.6 | 3/3 | 3 | 22.4 | 3/3 |
| 187.5 GCE/mL | 3 | 3 | 31.6 | 3/3 | 3 | 32.8 | 3/3 | 3 | 31.9 | 3/3 | 3 | 22.3 | 3/3 |
| 125 GCE/mL | 3 | 2 | 34.3 | 2/3 | 1 | 32.9 | 1/3 | 3 | 34.0 | 3/3 | 3 | 22.9 | 3/3 |
| 62.5 GCE/mL | 3 | 1 | 33.8 | 1/3 | 0 | UND | 0/3 | 2 | 35.7 | 2/3 | 3 | 22.9 | 3/3 |
| 7500 Dx gRNA | | | | | | | | | | | | | |
| 1000 GCE/mL | 3 | 3 | 29.5 | 3/3 | 3 | 30.2 | 3/3 | 3 | 29.9 | 3/3 | 3 | 22.6 | 3/3 |
| 500 GCE/mL | 3 | 3 | 31.7 | 3/3 | 2 | 31.8 | 2/3 | 3 | 31.5 | 3/3 | 3 | 23.3 | 3/3 |
| 187.5 GCE/mL | 3 | 2 | 32.0 | 2/3 | 2 | 35.5 | 2/3 | 3 | 31.9 | 3/3 | 3 | 22.5 | 3/3 |
| 125 GCE/mL | 3 | 1 | 36.0 | 1/3 | 0 | UND | 0/3 | 3 | 34.4 | 3/3 | 3 | 22.7 | 3/3 |
| 62.5 GCE/mL | 3 | 0 | UND | 0/3 | 0 | UND | 0/3 | 3 | 34.6 | 3/3 | 3 | 23.1 | 3/3 |
| QS5 Virus | | | | | | | | | | | | | |
| 1000 GCE/mL | 3 | 3 | 32.2 | 3/3 | 3 | 33.7 | 3/3 | 3 | 33.6 | 3/3 | 3 | 25.1 | 3/3 |
| 500 GCE/mL | 3 | 3 | 32.7 | 3/3 | 3 | 33.3 | 3/3 | 3 | 32.9 | 3/3 | 3 | 25.3 | 3/3 |
| 187.5 GCE/mL | 3 | 1 | 35.6 | 1/3 | 3 | 35.2 | 3/3 | 3 | 35.3 | 3/3 | 3 | 25.3 | 3/3 |

TABLE 15-continued

| Preliminary LoD | | | | | | | | | | | | | | |
|---|---|---|---|---|---|---|---|---|---|---|---|---|---|---|
| | | SARS-CoV-2 N Gene Positive | | | SARS-CoV-2 S Gene Positive | | | SARS-CoV-2 ORF1ab Positive | | | MS2 (Internal Control Positive) | | | |
| Target Level | Replicates | n | Mean $C_t$ | Detection Rate | n | Mean $C_t$ | Detection Rate | n | Mean $C_t$ | Detection Rate | n | Mean $C_t$ | Detection Rate | |
| 125 GCE/mL | 3 | 0 | UND | 0/3 | 0 | UND | 0/3 | 2 | 36.3 | 2/3 | 3 | 25.3 | 3/3 | |
| 62.5 GCE/mL | 3 | 0 | UND | 0/3 | 0 | UND | 0/3 | 0 | 38.4 | 0/3 | 3 | 25.5 | 3/3 | |
| QS5 gRNA | | | | | | | | | | | | | | |
| 1000 GCE/mL | 3 | 3 | 32.0 | 3/3 | 3 | 32.0 | 3/3 | 3 | 32.3 | 3/3 | 3 | 25.1 | 3/3 | |
| 500 GCE/mL | 3 | 3 | 34.5 | 3/3 | 2 | 35.9 | 2/3 | 3 | 34.2 | 3/3 | 3 | 25.5 | 3/3 | |
| 187.5 GCE/mL | 3 | 2 | 37.1 | 2/3 | 1 | 37.5 | 1/3 | 3 | 35.5 | 3/3 | 3 | 25.1 | 3/3 | |
| 125 GCE/mL | 3 | 1 | 37.2 | 1/3 | 1 | 35.1 | 1/3 | 3 | 34.7 | 3/3 | 3 | 24.9 | 3/3 | |
| 62.5 GCE/mL | 3 | 0 | 37.2 | 0/3 | 0 | UND | 0/3 | 0 | UND | 0/3 | 3 | 25.2 | 3/3 | |

UND: Undetermined Ct (no detectable Ct in any SARS-CoV-2 targets)

The initial LoD determination of the Super Pooling assay was 187.5 GCE/mL. The LoD was verified by testing 20 additional extraction replicates consisting of spiked SARS-COV-2 virus and spiked SARS-COV-2 viral genomic RNA into a matrix of pooled negative upper respiratory samples, extracted with the MagMAX kit on the KingFisher Flex instrument and tested on both the Applied Biosystems 7500 Fast Dx and QuantStudio 5 real-time PCR instruments using the same extracted RNA. Samples were spiked with SARS-COV-2 virus and SARS-COV-2 viral genomic RNA prior to extraction. Samples were extracted and tested with the Super Pooling assay on both the Applied Biosystems 7500 Fast Dx and QuantStudio 5 real-time PCR instruments using the same extracted RNA. The LoD of the 2D Pooling SARS-COV-2 was confirmed at 60 GCE/mL. Results are shown in Table 16 (Virus) and Table 17 (gRNA).

TABLE 16

| Confirmatory LoD (Virus) | | | | | | | | | | |
|---|---|---|---|---|---|---|---|---|---|---|
| | 7500 Dx | | | | | QuantStudio 5 | | | | |
| Replicate | MS2 Mean $C_t$ | N Gene Mean $C_t$ | S Gene Mean $C_t$ | ORF1ab Mean $C_t$ | Final Result | MS2 Mean $C_t$ | N Gene Mean $C_t$ | S Gene Mean $C_t$ | ORF1ab Mean $C_t$ | Final Result |
| 1 | 25.1 | 31.3 | 30.3 | 31.5 | POS | 24.9 | 31.5 | 32.3 | 33.5 | POS |
| 2 | 25.0 | 31.9 | 32.6 | 31.6 | POS | 25.0 | 33.0 | 33.5 | 33.9 | POS |
| 3 | 25.4 | 31.5 | 30.8 | 32.2 | POS | 25.1 | 31.4 | 33.3 | 34.1 | POS |
| 4 | 25.2 | 30.8 | 30.0 | 36.4 | POS | 25.2 | 31.7 | 35.1 | 34.6 | POS |
| 5 | 25.3 | 30.6 | 31.0 | 32.4 | POS | 25.6 | 32.5 | 33.3 | 33.9 | POS |
| 6 | 25.5 | 31.1 | 31.7 | 32.7 | POS | 25.8 | 36.3 | 34.8 | 33.9 | POS |
| 7 | 25.3 | 30.4 | 33.1 | 34.3 | POS | 25.6 | 34.1 | 34.8 | 33.0 | POS |
| 8 | 25.1 | 29.8 | 30.0 | 32.0 | POS | 25.5 | 32.8 | 32.8 | 34.4 | POS |
| 9 | 25.5 | 30.6 | 30.3 | 32.1 | POS | 25.6 | 33.3 | 33.3 | 33.7 | POS |
| 10 | 25.9 | 32.6 | 36.9 | 32.3 | POS | 25.8 | 33.5 | 33.3 | 35.7 | POS |
| 11 | 25.9 | 31.6 | 31.7 | 32.0 | POS | 25.6 | 30.9 | 33.2 | 33.9 | POS |
| 12 | 25.9 | 32.4 | 32.1 | 32.5 | POS | 25.7 | 32.6 | 32.8 | 35.5 | POS |
| 13 | 25.2 | 31.2 | 30.8 | 32.1 | POS | 25.2 | 31.0 | 32.8 | 34.5 | POS |
| 14 | 25.2 | 31.2 | 31.8 | 32.1 | POS | 25.1 | 31.0 | 34.6 | 32.9 | POS |
| 15 | 24.9 | 32.2 | 30.3 | 33.5 | POS | 25.0 | 33.5 | 33.8 | 34.2 | POS |
| 16 | 25.1 | 31.5 | 32.5 | 32.2 | POS | 25.4 | 31.9 | 33.9 | 33.9 | POS |
| 17 | 25.0 | 33.1 | 32.0 | 32.1 | POS | 25.0 | 35.1 | 35.3 | 35.2 | POS |
| 18 | 24.5 | 29.5 | 32.2 | 31.8 | POS | 24.9 | 31.6 | 33.0 | 34.4 | POS |
| 19 | 25.4 | 32.0 | 32.1 | 32.9 | POS | 25.2 | 33.5 | 33.5 | 35.9 | POS |
| 20 | 25.4 | 32.4 | 32.1 | 33.5 | POS | 25.2 | 33.0 | 33.0 | 35.5 | POS |
| Mean | 25.3 | 31.4 | 31.7 | 32.6 | N/A | 25.3 | 32.7 | 33.6 | 34.3 | N/A |
| Positive/Valid | 20/20 | 20/20 | 20/20 | 20/20 | 20/20 | 20/20 | 20/20 | 20/20 | 20/20 | 20/20 |
| Hitrate | 100% | 100% | 100% | 100% | 100% | 100% | 100% | 100% | 100% | 100% |

POS: Positive (two or more target positive)

TABLE 17

| Confirmatory LoD (gRNA) | | | | | | | | | | |
|---|---|---|---|---|---|---|---|---|---|---|
| | 7500 Dx | | | | | QuantStudio 5 | | | | |
| Replicate | MS2 Mean $C_t$ | N Gene Mean $C_t$ | S Gene Mean $C_t$ | ORF1ab Mean $C_t$ | Final Result | MS2 Mean $C_t$ | N Gene Mean $C_t$ | S Gene Mean $C_t$ | ORF1ab Mean $C_t$ | Final Result |
| 1 | 26.2 | 33.1 | 30.9 | 33.0 | POS | 29.4 | 34.6 | 36.8 | 33.7 | POS |
| 2 | 26.1 | UND | 30.9 | 33.2 | POS | 25.7 | 35.0 | 32.9 | 33.7 | POS |
| 3 | 25.8 | 33.3 | UND | 33.8 | POS | 25.8 | 36.7 | 39.0 | 34.8 | POS |
| 4 | 25.6 | 33.2 | 32.8 | 34.2 | POS | 25.8 | 35.5 | 33.8 | 34.2 | POS |
| 5 | 24.8 | 32.6 | 34.7 | 33.0 | POS | 24.8 | 33.9 | 33.9 | 34.8 | POS |
| 6 | 25.3 | 33.4 | 32.2 | 33.5 | POS | 25.1 | 33.6 | 35.0 | 35.1 | POS |
| 7 | 25.7 | 35.1 | 35.0 | 33.2 | POS | 25.1 | 34.3 | 32.9 | 34.0 | POS |
| 8 | 25.5 | 33.6 | 34.9 | 33.6 | POS | 24.9 | 32.9 | 31.9 | 34.9 | POS |
| 9 | 25.9 | 32.3 | 35.3 | 33.2 | POS | 25.4 | 32.5 | 34.1 | 34.9 | POS |
| 10 | 25.7 | 32.7 | 32.2 | 33.5 | POS | 25.4 | 34.0 | 32.7 | 34.4 | POS |
| 11 | 25.4 | 33.6 | UND | 33.2 | POS | 25.2 | 35.0 | 33.0 | 34.1 | POS |
| 12 | 25.4 | 33.5 | 34.6 | 33.8 | POS | 25.5 | 34.2 | 35.1 | 35.7 | POS |
| 13 | 25.5 | 37.0 | 37.1 | 34.4 | POS | 25.3 | 34.8 | 34.3 | 35.7 | POS |
| 14 | 25.5 | 33.8 | 37.9 | 32.5 | POS | 25.1 | 34.5 | 34.5 | 34.8 | POS |
| 15 | 26.0 | 33.7 | 37.6 | 33.9 | POS | 25.5 | 34.1 | 33.4 | 35.0 | POS |
| 16 | 26.0 | 33.1 | 34.9 | 33.3 | POS | 25.3 | 35.1 | 36.2 | 35.9 | POS |
| 17 | 25.5 | 33.9 | 32.1 | 33.3 | POS | 24.9 | 32.6 | 32.1 | 34.5 | POS |
| 18 | 25.4 | 31.8 | 33.6 | 33.7 | POS | 25.1 | 34.2 | 35.3 | 34.4 | POS |
| 19 | 25.1 | 33.8 | 31.3 | 33.0 | POS | 25.1 | 33.9 | 37.1 | 35.0 | POS |
| 20 | 25.1 | 36.1 | 31.7 | 33.6 | POS | 24.9 | 33.7 | 34.2 | 34.8 | POS |
| Mean | 25.6 | 33.7 | 33.9 | 33.4 | N/A | 25.5 | 34.3 | 34.4 | 34.7 | N/A |
| Positive/Valid | 20/20 | 19/20 | 15/20 | 20/20 | 20/20 | 20/20 | 20/20 | 18/20 | 20/20 | 20/20 |
| Hitrate | 100% | 955 | 75% | 100% | 100% | 100% | 100% | 90% | 100% | 100% |

UND: Undetermined Ct (no detectable Ct in any SARS-CoV-2 targets);
POS: Positive (two or more target positive)

All clinical samples have been previously confirmed in-house as a known negative. Details of the laboratory process are contained within Example 1.

Example 3: Clinical Evaluation Under Emergency Use Authorization (EUA)

The Super Pooling Assay is a real-time reverse transcription polymerase chain reaction (RT-PCR) test for the qualitative detection of nucleic acid from SARS-COV-2 in upper respiratory swab specimens from individuals suspected of COVID-19 by their healthcare provider. Super Pooling allows for up to 100 samples to be pooled into a single tube with little to no loss in sensitivity as compared to the ThermoFisher TaqPath COVID-19 RT-PCR Test.

This protocol outlines the clinical evaluation of 30 previously identified negative and 30 previously identified positive samples through the Super Pooling assay.

Experimental Design

Performance of the Super Pooling assay was evaluated using two 30 pool groups. The first looked at 30 pools consisting of 100 negative upper respiratory samples. The second looked at 30 pools consisting of 1 positive upper respiratory sample and 99 negative upper respiratory samples. For the second, the 30 pools were broken down as follows: (1) 6 pools with a positive sample Ct≤18 for all 3 targets (ORF1ab, N gene, S gene), (2) 8 pools with a positive sample with 18<Ct≤26 for all 3 targets (ORF1ab, N gene, S gene), (3) 8 pools with a positive sample with 26<Ct≤34 for all 3 targets (ORF1ab, N gene, S gene), and (4) 8 pools with a positive sample with 34<Ct≤37 for all 3 targets (ORF1ab, N gene, S gene)

Experimental Protocol

Samples were extracted with the MagMAX kit on the KingFisher Flex instrument and tested with the TaqPath COVID-19 kit on both the Applied Biosystems 7500 Fast Dx and QuantStudio 5 real-time PCR instruments using the same extracted RNA. The Ct's listed refer to TaqPath 200 μL media input protocol. In the case that there are insufficient positive clinical samples for a given Ct range, a higher concentration sample was diluted with saline into the listed range. Finally, to account for potential degradation during storage and thawing, all positive upper respiratory samples used in this study were retested unpooled with the TaqPath COVID-19 kit with 200 μL input according to 102279 Rev A PI, TaqPath COVID-19 Combo Kit in parallel with the super pooling assay.

All clinical samples were previously confirmed, in-house, as a known negative or positive using a SARS-Cov-2 diagnostic assay that has been internally validated and granted emergency use authorization by the FDA. Details of the laboratory process are described above.

Criteria for Success

For performance of the super pooling assay to be considered a success, two benchmarks were defined. First, at least 29 of 30 pools (95% negative percent agreement) consisting of 100 negative upper respiratory samples must be identified as negative. Second, at least 29 of 30 pools (95% positive percent agreement) consisting of 1 positive upper respiratory sample and 99 negative upper respiratory samples must be identified as positive.

Results

Figure 2:
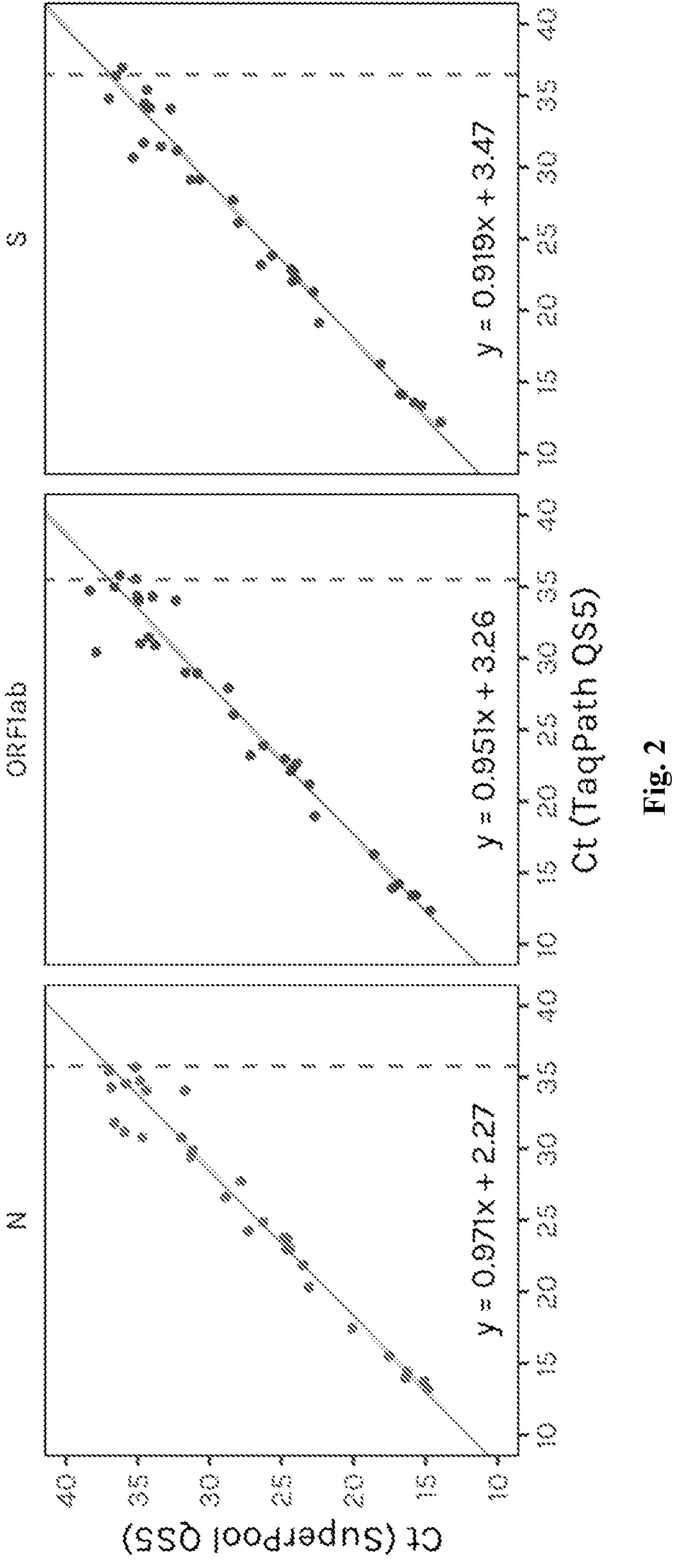
FIG. 2 shows the results of analyzing 100-plex pools of 1 positive upper respiratory sample and 99 negative upper respiratory samples analyzed by the ThermoFisher TaqPath™ Combo Kit EUA and super pooling methods on the QuantStudio 5. The diagonal line is the Passing-Bablok regression line; the vertical dashed line shows the equivalent TaqPath™ Ct when the regression equation (displayed on chart) is solved for a pooled Ct of 37.

All 30 pools consisting of 100 negative upper respiratory samples tested negative on the 7500 Fast Dx and QuantStudio 5. All 30 pools consisting of 1 positive upper respiratory sample and 99 negative upper respiratory samples tested positive on the 7500 Fast Dx. All 29 out of 30 pools consisting of 1 positive upper respiratory sample and 99 negative upper respiratory samples tested positive on the QuantStudio 5. Ct correlation plots for the 7500 Fast Dx are shown in FIG. 1. Ct correlation plots for the QuantStudio 5 are shown in FIG. 2. A summary of the Clinical Evaluation Study results are summarized in Tables 18-21.

TABLE 18

Summary of Passing-Bablok regression of Ct values for pooled samples tested with the Super Pooling workflow and the ThermoFisher TaqPath COVID-19 Combo kit standard workflow

| Instrument | Gene | Slope (95% CI) | Intercept (95% CI) | Equation | eqn solved for y = 37 | Ct Shift |
|---|---|---|---|---|---|---|
| 7500 | N | 1.019 (0.955, 1.096) | −0.240 (−1.934, 1.027) | y = 1.02 − 0.24 | 36.54 | −0.46 |
| | S | 0.989 (0.940, 1.077) | 1.163 (−0.330, 2.513) | y = 0.989x + 1.16 | 36.24 | −0.76 |
| | ORF1ab | 0.868 (0.764, 0.987) | 3.061 (−0.263, 6.401) | y = 0.868x + 3.06 | 39.12 | 2.12 |
| QS5 | N | 0.971 (0.910, 1.046) | 2.270 (−1.860, 3.606) | y = 0.971x + 2.27 | 35.77 | −1.23 |
| | S | 0.919 (0.864, 0.988) | 3.472 (2.130, 4.917) | y = 0.919x + 3.47 | 36.48 | −0.51 |
| | ORF1ab | 0.951 (0.894, 1.024) | 3.261 (1.972, 4.473) | y = 0.951x + 3.26 | 35.47 | −1.53 |

TABLE 19

Overall performance of Super Pooling workflow (run on 7500 Fast Dx) vs. TaqPath (standard workflow)

| | | Comparator (Individually Tested) | | |
|---|---|---|---|---|
| | | Positive | Inconclusive | Negative |
| Super Pooling 100-plex pools | Positive | 30 | 0 | 0 |
| | Inconclusive | 0 | 0 | 0 |
| | Negative | 0 | 0 | 30 |
| | PPA (95% CI) | 100% (88.65%-100%) | | |
| | NPA (95% CI) | 100% (88.65%-100%) | | |

TABLE 20

Overall performance of Super Pooling workflow (run on QuantStudio 5) vs. ThermoFisher TaqPath COVID-19 Combo Kit (standard workflow)

| | | Comparator (Individually Tested) | | |
|---|---|---|---|---|
| | | Positive | Inconclusive | Negative |
| Super Pooling 100-plex pools | Positive | 29 | 0 | 0 |
| | Inconclusive | 1 | 0 | 0 |
| | Negative | 0 | 0 | 30 |

TABLE 20-continued

Overall performance of Super Pooling workflow (run on QuantStudio 5) vs. ThermoFisher TaqPath COVID-19 Combo Kit (standard workflow)

| | Comparator (Individually Tested) | | |
|---|---|---|---|
| | Positive | Inconclusive | Negative |
| PPA[1] (95% CI) | 96.67% (83.30%-99.83%)* | | |
| NPA (95% CI) | 100% (88.65%-100%) | | |

*The inconclusive was treated as a negative for the PPA calculation.
[1]Includes non-negative samples.

In total, 30 unique positive samples in pools and 30 unique negative sample pools were tested through the Super Pooling workflow. For 100-sample pools run on the 7500 Fast Dx, this assay has a positive percent agreement (sensitivity) of 100% (95% CI: 88.65% to 100%) and a negative percent agreement (specificity) of 100% (95% CI: 88.65% to 100%). For 100-sample pools run on the QuantStudio 5, this assay has a positive percent agreement (sensitivity) of 96.67% (95% CI: 83.30% to 99.83%) and a negative percent agreement (specificity) of 100% (95% CI: 88.65% to 100%) as seen in Table 19 and Table 21. Clinical evaluation study analysis with pooled testing stratified by Ct of the positive samples can be found in Table 21.

TABLE 21

Positive samples tested in a 100-plex pool

| | | Super Pooling (100-plex pools) | | | |
|---|---|---|---|---|---|
| | | 7500 Fast Dx Pools with positive samples of Ct ≤ 18 | | QS5 Pools with positive samples of Ct ≤ 18 | |
| | | Positive | Negative | Positive | Negative |
| Comparator (individually tested) | Positive | 6 | 0 | 6 | 0 |
| | Negative | 0 | 0 | 0 | 0 |
| | | Pools with positive samples of 18 < Ct ≤ 26 | | Pools with positive samples of 18 < Ct ≤ 26 | |
| | | Positive | Negative | Positive | Negative |
| Comparator (individually tested) | Positive | 8 | 0 | 8 | 0 |
| | Negative | 0 | 0 | 0 | 0 |

TABLE 21-continued

| Positive samples tested in a 100-plex pool | | | | | |
|---|---|---|---|---|---|
| | | Pools with positive samples of 26 < Ct ≤ 34 | | Pools with positive samples of 26 < Ct ≤ 34 | |
| | | Positive | Negative | Positive | Negative |
| Comparator (individually tested) | Positive | 8 | 0 | 8 | 0 |
| | Negative | 0 | 0 | 0 | 0 |
| | | Pools with positive samples of 34 < Ct ≤ 37 | | Pools with positive samples of 34 < Ct ≤ 37 | |
| | | Positive | Negative | Positive | Negative |
| Comparator (individually tested) | Positive | 8 | 0 | 7 | 0 |
| | Negative | 0 | 0 | 0 | 0 |
| | Inconclusive | 0 | 0 | 1* | 0 |

*This positive sample would have been found during reflex testing of the inconclusive pool.

What is claimed is:

1. A method for detecting the presence of a nucleic acid in a pooled sample, the method comprising the steps of:
   (a) adding lysis buffer to a pooled sample to create a solution pool, wherein the pooled sample comprises two or more non-diluted test samples, and wherein the lysis buffer is added in an amount proportional to the number of individual samples;
   (b) adding nucleic acid binding beads to the solution pool, wherein, when the pooled sample comprises up to about 100 test samples, the amount of nucleic acid binding beads added is the amount used to analyze a single, individual test sample and this amount increases proportionately for every additional 100 samples or fraction thereof in the pooled sample;
   (c) concentrating the nucleic acid binding beads in the solution pool;
   (d) separating the nucleic acid binding beads from the solution pool;
   (e) washing the nucleic acid binding beads; and
   (f) analyzing the nucleic acid binding beads to detect the presence or absence of a nucleic acid.

2. The method of claim 1, further comprising:
   collecting two or more non-diluted test samples; and
   pooling the two or more individual non-diluted test samples to create the pooled sample, prior to lysing the pooled sample.

3. The method of claim 1, wherein the nucleic acid is a viral nucleic acid.

4. The method of claim 1, wherein the two or more samples are biological samples obtained from two or more individuals.

5. The method of claim 1, wherein the two or more samples are environmental samples.

6. The method of claim 1, wherein the number of non-diluted test samples in the pooled sample is at least two to about one hundred samples and the amount of nucleic acid binding beads added to the solution pool is about the amount used to analyze a single, individual sample.

7. The method of claim 1, wherein the number of non-diluted test samples in the pooled sample is about one hundred to about one thousand samples and the amount of nucleic acid binding beads added to the solution pool is between about one to about ten times the amount used to analyze a single, individual sample.

8. The method of claim 1, wherein the pooled sample comprises five or more non-diluted samples.

9. The method of claim 1, wherein the nucleic acid can be selected from a group comprising DNA or RNA.

10. The method of claim 9, wherein the RNA is SARS-COV-2 RNA.

11. The method of claim 4, wherein the pooled sample comprises cells from nasal swabs of the five or more individuals.

12. The method of claim 1, wherein the lysis buffer contains a buffering salt and/or an ionic salt.

13. The method of claim 12, wherein the lysis buffer further comprises a detergent.

14. The lysis buffer of claim 12, wherein the buffering salt is selected from a group consisting of: MPS, DPS, Tris-HCl, and HEPES-NaOH.

15. The lysis buffer of claim 12, wherein the ionic salt is selected from a group consisting of: NaCl, KCl, and $(NH_4)_2SO_4$.

16. The lysis buffer of claim 13, wherein the detergent is selected from a group consisting of: Triton X-100, TWEEN, and CHAPS.

17. The method of claim 1, wherein the separation step comprises magnetic separation, centrifugation, or column filtration.

18. The method of claim 1, wherein analyzing comprises polymerase chain reaction (PCR).

19. The method of claim 18, wherein the method comprises quantitative or endpoint PCR.

20. The method of claim 1, wherein analyzing comprises sequencing the nucleic acid adhered to the nucleic acid binding beads.

21. The method of claim 1, wherein the nucleic acid adhered to the beads is eluted for the analyzing step.

22. The method of claim 4, further comprising:
   obtaining a test sample from the at least two or more individuals, if the nucleic acid is detected in the pooled sample; and
   detecting the presence of the nucleic acid in one or more of the individual test samples.

23. The method of claim 22, wherein the nucleic acid is a viral nucleic acid.

* * * * *